United States Patent [19]

Cho et al.

[11] Patent Number: 5,463,046

[45] Date of Patent: Oct. 31, 1995

[54] 1-β-METHYL-2-THIOLIC CARBAPENEM DERIVATIVES

[75] Inventors: Jung H. Cho, Seoul; Chang H. Oh, Kyeonggi; Ki H. Nam, Seoul, all of Rep. of Korea

[73] Assignees: Dong Kook Pharmaceutical Co., Ltd.; Ki-Beom Kwon, both of Seoul, Rep. of Korea

[21] Appl. No.: 155,477

[22] Filed: Nov. 19, 1993

[51] Int. Cl.⁶ .................... C07D 487/04; A61K 31/40
[52] U.S. Cl. .................................................... 540/350
[58] Field of Search ........................ 540/350; 514/210

[56]  References Cited

U.S. PATENT DOCUMENTS

| | | | |
|---|---|---|---|
| 5,093,328 | 3/1992 | Sunagawa et al. | 514/210 |
| 5,227,376 | 7/1993 | Sunagawa et al. | 514/210 |
| 5,310,735 | 5/1994 | Kawamoto et al. | 540/350 |

OTHER PUBLICATIONS

Chemical abstracts vol. 122: 160367 (1995).
Chemical abstracts vol. 120: 322991(1994).
Chemical abstracts vol. 108: 150152 (1988).

*Recent Advances in The Chemistry Of β–Lactam Antibiotics,* Fourth International Symposium, P. H. Bentley and R. Southgate, eds., "Novel Carbapenems," T. N. Salzmann, et al., pp. 171 to 173. (Apr. 30, 1989).

*Primary Examiner*—Nicholas Rizzo
*Attorney, Agent, or Firm*—Morgan & Finnegan

[57]  ABSTRACT

The present invention relates to new 1-β-methyl-2-thiolic carbapenem derivatives represented by the following general formula (I) and producing method thereof.

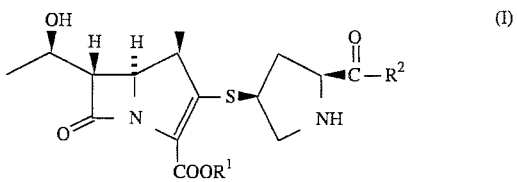

The above-mentioned compound is very stable against DHP-1 enzyme due to effective shielding of carbapenem ring structually and is highly effective in both gram-positive and gram-negative microorganism, especially has a remarkable effect on the *Pseudomonas aeruginosa* known as a disease germ having strong resistance.

3 Claims, No Drawings

1-β-METHYL-2-THIOLIC CARBAPENEM DERIVATIVES

BACKGROUND OF THE INVENTION

1. Field of the invention

The present invention relates to new 1-β-methyl-2-thiolic carbapenem derivatives represented by the following general formula (I)

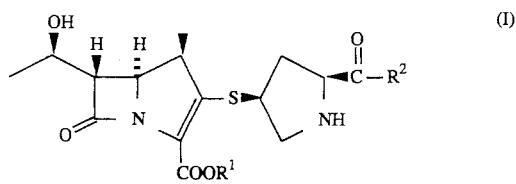

In the formula (I), $R^1$ denotes hydrogen or anion; when $R^1$ is hydrogen, $R^2$ denotes 2-hydroxyethylamino, 3-hydroxypropylamino, 2-(R)-hydroxypropylamino, 2-(S)-hydroxypropylamino, 2-(R)-hydroxybutylamino, 2-(S)-hydroxybutylamino, 4-hydroxybutylamino, 1-hydroxymethylpropyl-(R)-amino, 1-hydroxymethylpropyl-(S)-amino, 5-hydroxypentylamino, 1-isopropyl-2-hydroxyethyl-(R)-amino, 1-isopropyl-2-hydroxyethyl-(S)-amino, 6-hydroxyhexylamino, 1-(1-methylpropyl)-2-hydroxyethyl-(S)-amino, 1-(2-methylpropyl)-2-hydroxyethyl-(R)-amino, 1-(2-methylpropyl)-2-hydroxyethyl-(S)-amino, 2-(1,3-dihydroxypropyl)amino, 2,3-dihydroxypropylamino, N-(4-hydroxypiperidino), N-(2-hydroxymethylpiperidino), N-(2-hydroxyethylpiperidino), N-(3,3-dimethylpiperidino), N-(3-methylpiperidino), N-(1,2,5,6-tetrahydropyridinyl), N-(2-hydroxymethylpyrrolidino), N-homopiperidino, N-thiazoyl, N-thiomorpholinyl or N-(3-hydroxymethylthiazolyl); and when $R^1$ is anion, $R^2$ denotes N-(S-alkylthiomorpholinylium) of following general formula (①) or N-(S-alkylthiazolium) cation of following general formula).

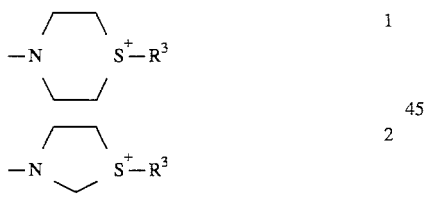

(In the above formula ① and ②, $R^3$ denotes methyl or low alkyl group of $C_2$–$C_4$)

2. Description of the prior art

The well-known compound among the carbapenem antibiotics which is a subject compound of the present invention is an antibiotic thienamycine which is produced by incubating special Streptomyces species and is active against both gram-positive and gram-negative bacteria. (Reference to the U.S. Pat. No. 3,950,357, Kahan et.al.). But, there was a defect such that this compound was decomposed by an enzyme named Dehydropeptidase-1 (DHP-1), so that the effect of this compound was decreased.

To solve the above problem, the method in which a inhibitor of DHP-1 enzyme named cilastatine is used together with a thienamycine was suggested by MERCK and CO., Inc. (Reference to the European Patent No. 48,301), but there was a still problem for using this composite of cilastatine and thienamycine.

SUMMARY OF THE INVENTION

Therefore, with concern the aforementioned problem, present inventors have studied for a long time to provide carbapenem antibiotics which are stable against DHP-1 enzyme and have synthesized new 1-β-methyl-2-thiolic carbapenem derivatives(I) having β-methyl group on the carbapenem ring. Also, present inventors have found that this new compound is very stable against the DHP-1 enzyme and is highly effective in both gram-positive and gram-negative microorganism, especially has a remarkable effect on the *Pseudomonas aeruginosa* known as a disease germ having strong resistance and that this effect arises from effective shielding of carbapenem ring by β-methyl group in 1-β-methyl-carbapenem derivatives(I).

In the present invention, the carbapenem ring in 1-β-methyl- 2-thiolic carbapenem derivatives having general formula (I) has 4 chiral carbon atoms and the maximum number of optical isomer configuration that can exist is $16(=2^4)$. Among these optical isomer configurations, especially (1R, 5S, 6S,8R)-configuration represented by following formula is superior to in vivo activity.

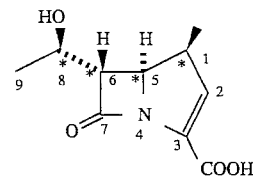

Also, in the 1-β-methyl-2-thiolic carbapenem derivatives (I) according to the present invention, thiol derivatives substituted on C-2 position of carbapenem ring show the optical isomerism according to circumstance and the maximum number of optical isomer configuration that can exist is $4(=2^2)$. Among these optical isomer configurations, especially (3S, 5S)-configuration represented by following formula shows remarkable effect in vivo activity.

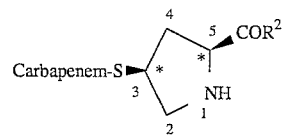

1-β-methyl-2-thiolic carbapenem derivatives (I) according to the present invention can be prepared by, for example, following reaction procedure:

(1) a step for producing a following compound (III) by reaction of compound (II) as a starting material with diphenyl chlorophosphate or trifluoromethanesulfonic anhydride in the present of a base,

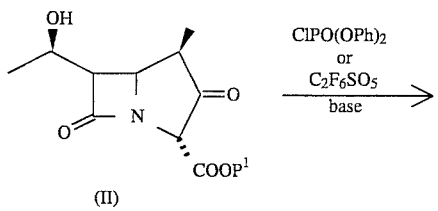

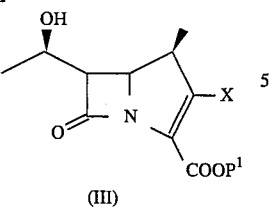

(III)

(In the above formula (II) and (III), $p^1$ denotes a —COOH protecting group and X denotes —OPO(OPh)$_2$ or —OSOOCF$_3$)

(2) a step for producing a protected carbapenem having following general formula (V) by reaction of the above compound (III) with thiol derivatives having following general formula (IV) in the present of a base, and

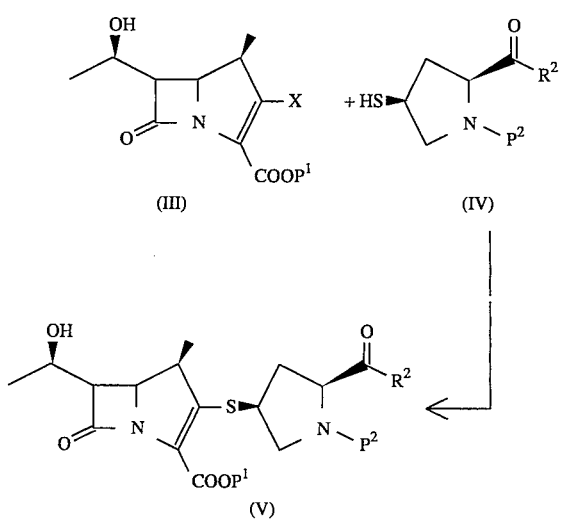

(In the above formula (IV) and (V), $R^2$ is the same as defined in formula (I) and $p^2$ denotes an amine protecting group)

(3) a step for producing the 1-β-methyl-2-thiolic carbapenem derivatives (I) by adding an organic solvent, phosphate or 4-MOPS buffer solution and palladium-on-charcoal catalyst into said protected carbapenem (V) in sequence and eliminating the protecting group by injecting with hydrogen.

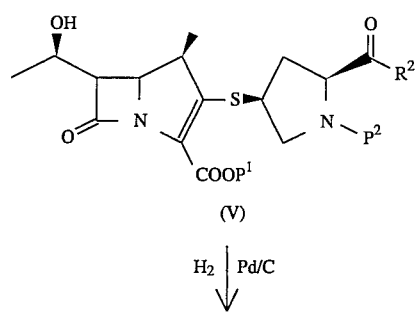

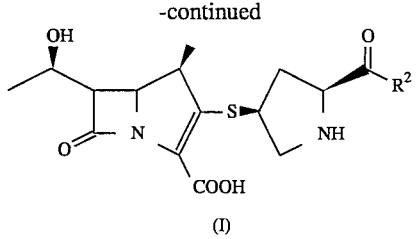

(I)

In the process of the present invention, the group $p^1$ is a protecting group which is generally used for protecting —COOH and, for example, is p-nitrobenzyl or allyl group. The group $P^2$ is a protecting group which is used for protecting amine and, for example, is p-nitrobenzyloxycarbonyl group.

Also, in 1-β-methyl-2-thiolic carbapenem derivatives (I) according to the present invention, the compound in which $R^1$ group is anion can be produced by forming a cation on $R^2$ position of protected carbapenem(V) obtained from step (2) by alkylation reaction, which followed by step (3) in which said protecting group is eliminated. For example, zwitter-ionic 1-β-methyl-2-thiolic carbapenem derivatives (I) in which $R^2$ is N-(S-alkylthiomopholinylium) can be produced by following reaction mechanism.

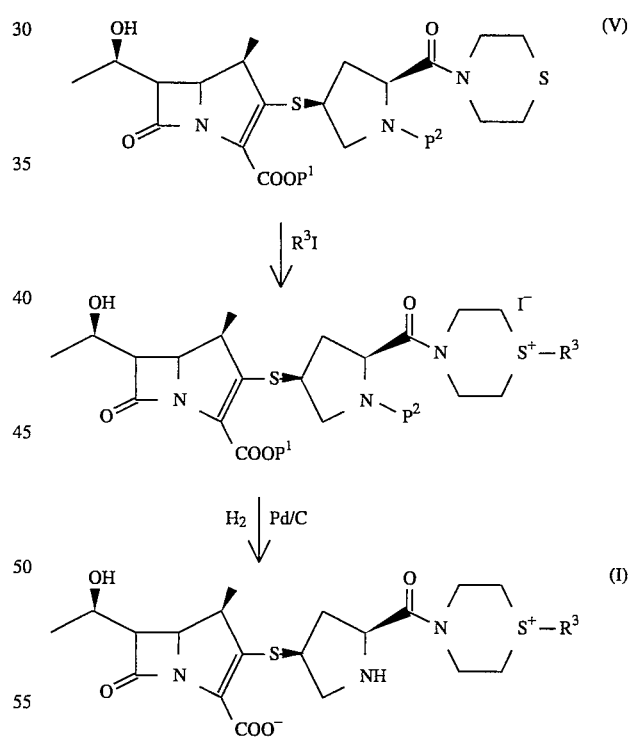

(in this formula, $R^3$ denotes methyl or low alkyl group of $C_2$-$C_4$)

Zwitter-ionic 1-β-methyl-2-thiolic carbapenem derivatives(I) synthesized by above-mentioned method Is generally quite soluble in water. $R^2$ which is suitable for forming a cation by alkylation reaction is N-thiazolyl or N-thiomorpholinyl group. In the above-mentioned alkylation reaction, conventional alkylating agents can be used and for example, methyl trifluoromethanesulfonate and alkyl halide such as methyl iodide are preferable.

DETAILED DESCRIPTION OF THE PREFERRED EMBODIMENTS

Hereinafter, the present invention will be further described by referring to the following example.

EXAMPLE 1

Preparation of p-nitrobenzyl(1R, 5S,6S)-2-[(3S,5S)-5-(thiomorpholinyl-N-carbonyl)-1-(p-nitrobenzyloxycarbonyl)pyrrolidine-3-ylthio]-6-[(R)-1-hydroxyethyl]-1-methylcarbapene,-3-carboxylate (4R,5R,6S,8R)-p-nitrobenzyl-4-methyl-6-(1-hydroxyethyl)-1-azabicyclo-(3.2.0)heptane-3,7-dione-2-carboxylate(2.0 g, 0.0055 mol) solution in acetonitrile was cooled down to 0° C. under the nitrogen atmosphere and was treated with diphenyl chlorophosphate(0.96 ml, 0.006 mol) in N,N-diisopropylethylamtne(0.82 ml, 0.006 mol). Thus-obtained mixture was agitated for 20 min. at 5° C. and cooled down to −20° C. and then added N,N-diisopropylethylamine (0.82 ml, 0.006 mol) and thiol compound (2.26 g, 0.0055 mol). This reaction mixture was agitated for 1 hour at −20° C. and further agitated for 30 min. at 0° C. 50 ml of ethylacetate was added to the reaction mixture and organic layer thereof was washed with 10% $NaHCO_3$ and saline solution and dried using anhydrous $MgSO_4$. The target material was obtained by removing an organic solvent and separating through a silica gel column. $^1$H-NMR($CDCl_3$): δ1.15(d, 3H, β-$CH_3$), 1.25(d, 3H, $CH_3$CHOH), 2.10, 2.80(m, 1H, pyrr.H), 2.84–295 (bs, 4H), 3.35(dd, 1H, $C_6$-H), 3.40–3.53(bs, 5H), 3.55(m, 1H, pyrr.H), 4.15(bs, 2H, pyrr.H), 4.18(dd, 1H, $C_5$-H), 4.25(quintet, 1H, $CH_3$CHOH), 4.75(m, 1H, pyrr.H), 5.25–5.40(quintet, 2H), 7.53(d, 4H), 7.65(d, 2H), 8.15(d, 2H)

EXAMPLE 2

Preparation of (1R,5S,6S)-6-[(R)-1-hydroxymethyl]-2[(3S,5S)-5-((S-methylthiomorpholinyl)amino-N-carbonyl)pyrrolidine-3-ylthio]-1-methyl carbapenem-3-carboxylic acid p-nitrobenzyl-(1R,5S,6S)-2-[(3S,5S)-5-(thiomorpholinyl-N-carbonyl)-1-(p-nitrobenzyloxycarbonyl)pyrrolidine-3-ylthio]-6-[(R)-1-hydroxyethyl]-1-methylcarbapenem-3-carboxylate(1.0 g, 0.0013 mol) solution in anhydrous dichloromethane(20 ml) was treated with methyl trifluoro methanesulfonate(0.40 ml, 0.0013 mol). The foamy solid compound was obtained by agitating for 2 hours at room temperature and removing the solvent. In this solid compound, tetrahydrofuran(20 ml), saline buffer solution(pH=7)(20 ml) and palladium-on-charcoal catalyst 1.0 g were added in sequence. Thus-obtained mixture was put into the hydrogen injector and shaken well for 1 hour. The mixture was filtered with a celite and filtrate was washed twice with ethylether. The target material was obtained by freeze-drying the water layer and separating by column of Diaion HP-20(trade name of an ion-exchange resin manufactured by Mitsubishi Chemical Industries Limited.).

$^1$H-NMR($D_2O$): δ1.22(d, 3H, β-$CH_3$), 1.26(d, 3H, $CH_3$CHOH), 2.10, 3.05(m, 1H, pyrr.H), 3.08–3.11(bs, 4H), 3.05(s, 3H), 3.30(dq, 1H, $C_1$-H) 3.35–3.55(bs, 5H), 3.95–4.10(bs, 2H, pyrr.H), 4.25–4.30(m, 2H), 4.45(m, 1H, pyrr.H)

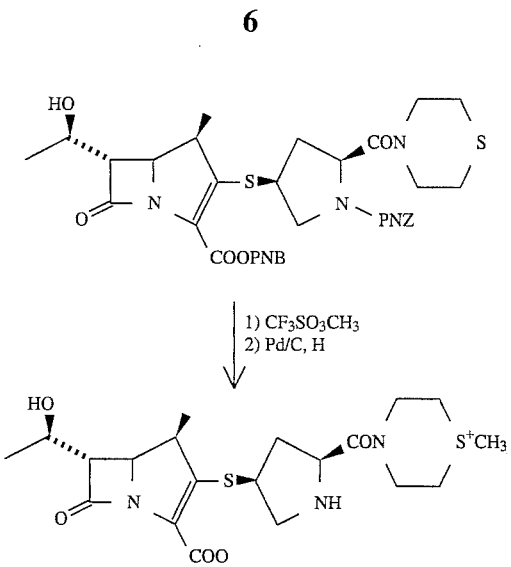

EXAMPLE 3

Preparation of (1R,5S,6S)-6-[(R)-1-hydroxyethyl]-2[(3S,5S)-5-((2-hydroxyethyl)aminocarbonyl)pyrrolidine-3-ylthio]-1-methylcarbapenem-3carboxylic acid (4R,5R,6S,8R) p-nitrobenzyl-4-methyl-6-(1-hydroxyethyl)-1-azabicyclo-(3.2.0)heptane-3,7-dione-2-carboxylate(2.0 g, 0.0055 mol) solution in acetonitrile (20 ml) was cooled down to 0° C. under nitrogen atmosphere and treated with N,N-diisopropylethylamine(0.82 ml, 0.006 mol) and diphenyl chlorophosphate(0.96 ml, 0.006 mol). Thus-obtained mixture was agitated for 30 min at 5° C. and cooled down to −20° C. and then added N,N-diisopropylethylamine (0.82 ml, 0.006 mol) and (2S,4S)-2-(2-hydroxyethyl)aminocarbonyl-4-mercapto-1-p-nitrobenzyloxycarbonylpyrrolidine(2.26 g, 0.0055 mol). The reaction mixture was agitated for 1 hour at −20 ° C. and further agitated 30 min. at 0° C. The reaction mixture was added 50 ml of ethyl acetate and washed organic layer with 10% $NaHCO_3$ and saline solution and dried using anhydrous $MgSO_4$. The material was obtained by removing an organic layer from the mixture and separating through the silica gel column. In this solid compound, tetrahydrofuran(20 ml), saline buffer solution(pH=7, 20 ml) and palladium-on-charcoal catalyst 1.0 g were added in sequence, and this mixture was put into hydrogen injector and shaken well for 1 hour. The reaction mixture was filtered using a celite and washed twice with ethyl ether (20 ml). The target material was obtained by freeze-drying the water layer and separating by column of Diaion HP-20.

$^1$H-NMR($D_2O$): δ1.19(d, 3H, β-$CH_3$), 1.28(d, 3H, $CH_3$CHOH), 2.02, 2.83(m, 1H, pyrr.H), 3.30–3.48(m, 5H, CONH$CH_2$, pyrr.H, $C_6$-H and $C_1$-H), 3.63–3.70(m, 3H, pyrr.H and $CH_2$OH), 3.97(m, 1H, pyrr.H), 4.25–4.31(m, 2H, $C_5$-H and $CH_3$CHOH), 4.35(t, 1H, pyrr.H)

EXAMPLE 4

Preparation of (1R,5S,6S)-6-[(R)-1-hydroxyethyl]-2-[(3S,5S)-5-((3-hydroxypropyl)aminocarbonyl)pyrrolidine-3-ylthio]-1-methylcarbapenem-3 -carboxylic acid The procedure was carried out according to the Example 3 and the used thiol compound was (2S,4S)-2-(3-hydroxypropyl)aminocarbonyl-4-mercapto-1-p-nitrobenzyloxycarbonyl pyrrolidine.

¹H-NMR(D₂O): δ1.19(d, 3H, β-CH₃), 1.22(d, 3H, CH₃CHOH), 2.05, 2.87(m, 1H, pyrr.H), 3.29–3.46(m, 5H, CONHCH₂, pyrr.H, C₆-H and C₁-H), 3.61–3.70(m, 3H, pyrr.H and CH₂OH), 3.97(m, 1H, pyrr.H), 4.20–4.31(m, 2H, C₅-H and CH₃CHOH), 4.35(t, 1H, pyrr.H)

EXAMPLE 5

Preparation of
(1R,5S,6S)-6-[(R)-1-hydroxyethyl]-2-[(3S,5S)-5-((2-(R)-hydroxypropyl)aminocarbonyl)pyrrolidine-3-ylthio]-1-methylcarbapenem-3-carboxylic acid The Procedure was carried out according to the Example 3 and the used thiol compound was (2S,4S)-2-(2-(R)-hydroxypropyl)aminocarbonyl-4-mercapto-1-p-nitrobenzyloxycarbonyl pyrrolidine.

¹H-NMR(D₂O): δ1.15–1.21(dd, 6H, CH₃ and β-CH₃), 1.26(d, 3H, CH₃ CHOH), 2.05, 2.93(m, 1H, pyrr.H), 3.20–3.48(m, 5H, CONHCH₂, pyrr.H, C₆-H and C₁-H), 3.87(m, 1H, pyrr.H), 3.91–4.08(m, 2H, pyrr.H and CHOH), 4.18–4.28(m, 2H, C₅-H and CH₃CHOH), 4.50(t, 1H, pyrr.H)

EXAMPLE 6

Preparation of
(1R,5S,6S)-6-[(R)-1-hxdroxyethyl]-2-[(3S,5S)-5-((2-(S)-hydroxypropyl)aminocarbonyl)pyrrolidine-3-ylthio]-1-methylcarbapenem-3-carboxylic acid The procedure was carried out according to the Example 3 and the used thiol compound was (2S,4S)-2-(2-(S)-hydroxypropyl)aminocarbonyl-4-mercapto-1-p-nitrobenzyloxycarbonyl pyrrolidine.

¹H-NMR(D₂O): δ1.17–1.23 (dd, 6H, CH₃ and β-CH₃), 1.27(d, 3H, CH₃CHOH), 2.05, 2.89(m, 1H, pyrr.H), 3.20–3.51(m, 5H, CONHCH₂, pyrr.H, C₆-H and C₁-H), 3.77(m, 1H, pyrr, H), 3.91–4.10(m, 2H, pyrr.H and CHOH), 4.18–4.28(m, 2H, C₅-H and CH₃CHOH), 4.50(t, 1H, pyrr.H)

EXAMPLE 7

Preparation of
(1R,5S,6S)-6-[(R)-1-hydroxyethyl]-2-[(3S,5S)-5-((2-(R)-hydroxybutyl)aminocarbonyl)pyrrolidine-3-ylthio]-1-methylcarbapenem-3-carboxylic acid The procedure was carried out according to the Example 3 and the used thiol compound was (2S,4S)-2-[2-(R)-hydroxybutyl]aminocarbonyl-4-mercapto-1-p-nitrobenzyloxycarbonyl pyrrolidine.

¹H-NMR(D₂O): δ1.15 (t, 3H, -CH₃), 1.19(d, 3H, β-CH₃), 1.28(d, 3H, CH₃CHOH), 2.05, 2.90(m, 1H, pyrr.H), 3.37–3.48(m, 3H, CH₂CH₃ and C₁-H), 3.53–3.62(m, 2H, pyrr.H and C₆-H), 3.75(m, 1H, pyrr.H), 3.94–4.08(m, 2H, pyrr.H and CHOH), 4.25–4.31(m, 2H, C₅-H and CH₃CHOH), 4.35(t, 1H, pyrr.H)

EXAMPLE 8

Preparation of
(1R,5S,6S)-6-[(R)-1-hydroxyethyl]-2-[(3S,5S)-5-((2-(S)-hydroxybutyl)aminocarbonyl)pyrrolidine-3-ylthio]-1-methylcarbapenem-3-carboxylic acid The procedure was carried out according to the Example 3 and the used thiol compound was (2S,4S)-2-(2-(S)-hydroxybutyl)aminocarbonyl-4-mercapto-1-p-nitrobenzyloxycarbonyl pyrrolidine.

¹H-NHR(D₂O): δ1.15 (t, 3H, -CH₃), 1.19(d, 3H, β-CH₃), 1.29(d, 3H, CH₃CHOH), 2.05, 2.93(m, 1H, pyrr.H), 3.38–3.54(m, 3H, CH₂CH₃ and C₁-H), 3.57–3.68(m, 2H, pyrr.H and C₆-H), 3.75(m, 1H, pyrr.H), 3.94–4.10(m, 2H, pyrr.H and CHOH), 4.22–4.35(m, 2H, C₅-H and CH₃CHOH), 4.45(t, 1H, pyrr.H)

EXAMPLE 9

Preparation of
(1R,5S,6S)-6-[(R)-1-hydroxyethyl]-2-[(3S,5S)-5-((4-hydroxybutyl)aminocarbonyl)pyrrolidine-3-ylthio]-1-methylcarbapenem-3-carboxylic acid The procedure was carried out according to the Example 3 and the used thiol compound was (2S,4S)-2-(4-hydroxybutyl)aminocarbonyl-4-mercapto-1-p-nitrobenzyloxycarbonyl pyrrolidine.

¹H-NMR(D₂O): δ1.19(d, 3H, β-CH₃), 1.24(d, 3H, CH₃CHOH), 1.51–1.62(bs, 4H, CH₂CH₂C₂OH), 2.05, 2.93(m, 1H, pyrr.H), 3.18–3.50(m, 5H, CONHCH₂, pyrr.H, C₆-H and C₁-H), 3.55(bs, 2H, CH₂CH₂OH), 3.77(m, 1H, pyrr.H), 4.05(m, 1H, pyrr.H), 4.25–4.31(m, 2H, C₆-H and CH₃CHOH), 4.45(t, 1H, pyrr.H)

EXAMPLE 10

Preparation of
(1R,5S,6S)-6-[(R)-1-hydroxyethyl]-2-[(3S,5S)-5-((1-hydroxymethyl)propyl-(R)-aminocarbonyl)pyrrolidine-3-ylthio]-1-methylcarbapenem- 3-carboxylic acid The procedure was carried out according to the Example 3 and the used thiol compound was (2S,4S)-2-(1-hydroxymethyl)propyl-(R)-aminocarbonyl-4-mercapto-1-p-nitrobenzyloxycarbonyl pyrrolidine.

¹H-NMR(D₂O): δ0.90–0.99 (t, 3H, CH₃), 1.19(d, 3H, β-CH₃), 1.29(d, 3H, CH₃CHOH), 1.90(m, 1H, CH), 2.08, 2.99(m, 1H, pyrr.H), 3.30–3.68(m, 4H, CONHCH, pyrr.H, C₆-H and C₁-H), 3.73–3.95(m, 4H, pyrr.H and CH₂OH), 4.08(m, 1H, pyrr.H), 4.25–4.31(m, 2H, C₅-H and CH₃ CHOH), 4.55(t, 1H, pyrr.H)

EXAMPLE 11

Preparation of
(1R,5S,6S)-6-[(R)-1-hydroxyethyl]-2-[(3S,5S)-5-((1-hydroxymethyl)propyl-(S)-aminocarbonyl)pyrrolidine-3-ylthio]-1-methylcarbapenem-3-carboxylic acid The procedure was carried out according to the Example 3 and the used thiol compound was (2S,4S)-2-(1-hydroxymethyl)propyl-(S)-aminocarbonyl-4-mercapto- 1-p-nitrobenzyloxycarbonyl pyrrolidine.

¹H-NMR(D₂O): δ0.90–0.98 (t, 3H, CH₃), 1.19(d, 3H, β-CH₃), 1.29(d, 3H, CH₃CHOH), 1.90(m, 1H, CH), 2.08, 2.99(m, 1H, pyrr.H), 3.30–3.68(m, 4H, CONH$\underline{CH}$, pyrr.H, C$_6$-H and C$_1$-H), 3.73–3.95(m, 4H, pyrr.H and $\overline{CH_2OH}$), 4.08(m, 1H, pyrr.H), 4.25–4.31(m, 2H, C$_5$-H $\overline{and}$ CH$_3$ $\underline{CHOH}$), 4.55(t, 1H, pyrr.H)

EXAMPLE 12

Preparation of
(1R,5S,6S)-6-[(R)-1-hydroxyethyl]-2-[(3S,5S)-5-((
5-hydroxypentyl)aminocarbonyl)pyrrolidine-3-ylthio]-
1-methylcarbapenem-3-carboxylic acid The procedure was carried out according to the Example 3 and the used thiol compound was (2S,4S)-2-(5-hydroxypentyl)aminocarbonyl-4-mercapto-1-p-nitrobenzyloxycarbonyl pyrrolidine.

$^1$H-NMR(D$_2$O): δ1.19(d, 3H, β-CH$_3$), 1.25(d, 3H, CH$_3$CHOH), 1.52–1.73(m, 6H, 3CH$_2$), 2.02, 2.89(m, 1H, $\overline{pyrr.H}$), 3.21–3.48(m, 5H, CONHCH$_2$, pyrr.H, C$_6$-H and C$_1$-H), 3.58(bs, 2H, CH$_2$CH$_2$OH), 3.80(m, 1H, pyrr.H), 4.08(m, 1H, pyrr.H), 4.25(m, 2H, CH$_5$-H and CH$_3$ $\underline{CHOH}$), 4.45(t, 1H, pyrr.H)

EXAMPLE 13

Preparation of
(1R,5S,6S)-6-[(R)-1-hydroxethyl]-2-[(3S,5S)-5-((
1-isopropyl-2-hydroxyethyl)-(R)-aminocarbonyl)pyrrolidine-3-ylthio]-1-methylcarbapenem-3-carboxylic
acid The procedure was carried out according to the Example 3 and the used thiol compound was (2S,4S)-2-(1-isopropyl-2-hydroxyethyl)-(R)-aminocarbonyl)-4-mercapto-1-p-nitrobenzyloxycarbonyl pyrrolidine.

$^1$H-NMR(D$_2$O): δ0.90–0.98(m, 6H, 2CH$_3$), 1.19(d, 3H, β-CH$_3$), 1.29(d, 3H, CH$_3$CHOH), 1.90(m, 1H, CH) 2.08, 2.99(m, 1H, pyrr.H), $\overline{3.30}$–3.68(m, 4H, CONH$\underline{CH}$, pyrr.H, C$_6$-H and C$_1$-H), 3.73–3.95(m, 4H, pyrr.H and $\overline{CH_2OH}$), 4.08(m, 1H, pyrr.H), 4.25–4.31(m, 2H, C$_5$-H $\overline{and}$ CH$_3$ $\underline{CHOH}$), 4.55(t, 1H, pyrr.H)

EXAMPLE 14

Preparation of
(1R,5S,6S)-6-[(R)-1-hydroxyethyl]-2-[(3S,5S)-5-(
1-isopropyl-2-hydroxyethyl)-(S)-aminocarbonyl)pyrrolidine-3-ylthio]-1-methylcarbapenem- 3-carboxylic acid The procedure was carried out according to the Example 3 and the used thiol compound was (2S,4S)-2-(1-isopropyl-2-hydroxyethyl)-(S)-aminocarbonyl)-4-mercapto-1-p-nitrobenzyloxycarbonyl pyrrolidine.

$^1$H-NMR(D$_2$O): δ0.09–0.98(m, 6H, 2Ch$_3$), 1.19(d, 3H, β-CH$_3$), 1.29(d, 3H, CH$_3$CHOH, 1.90(m, 1H, CH), 2.08, 2.99(m, 1H, pyrr.H), $\overline{3.30}$–3.68(m, 4H, CONH$\underline{CH}$, C$_6$-H and C$_1$-H), 3.73–3.95(m, 4H, pyrr.H and $\overline{CH_2OH}$), 4.25–4.31(m, 2H, C$_5$-H and CH$_3$$\underline{CHOH}$), 4.55(t, 1$\overline{H, pyrr.H}$)

EXAMPLE 15

Preparation of
(1R,5S,6S)-6-[(R)-1-hydroethyl]-2-[3S,5S)-5-((
6-hydroxyhexyl)aminocarbonyl)pyrrolidine-3-ylthio]-
1-methylcarbapenem-3-carboxylic acid.

The procedure was carried out according to the Example 3 and the used thiol compound was (2S,4S)-2-(6-hydroxypropyl)aminocarbonyl-4-mercapto- 1-p-nitrobenzyloxycarbonyl pyrrolidine.

$^1$H-NMR(D$_2$O): δ1.18(d, 3H, β-CH$_3$), 1.2(d, 3H, CH$_3$CHOH), 1.52–1.80(m, 8H, 4CH$_2$), 2.05, 2.90(m, 1H, $\overline{pyrr.H}$), 3.20–3.51(m, 5H, CONHCH$_2$, pyrr.H, C$_6$-H and C$_1$-H), 3.55(bs, 2H, CH$_2$CH$_2$OH) $\overline{3.81}$(m, 1H, pyrr.H), 4.05(m, 1H, pyrr.H), 4.25$\overline{-4.31}$ (m, 2H, C$_5$-H and CH$_3$ $\underline{CHOH}$), 4.45(t, 1H, pyrr.H)

EXAMPLE 16

Preparation of
(1R,5S,6S)-6-[(R)-1-hydroxyethyl]-2-[(3S,5S)-5-((
1-isobutyl-2-hydroxyethyl-(R)-aminocarbonyl)pyrrolidine-3-ylthio]-1-methylcarbapenem-3-carboxylic
acid The procedure was carried out according to the Example 3 and the used thiol compound was (2S,4S)-2-(1-isobutyl-2-hydroxyethyl)aminocabonyl- 4-mercapto-1-p-nitrobenzyloxycarbonyl pyrrolidine.

$^1$H-NMR(D$_2$O): δ0.85–0.96(m, 6H, 2CH$_3$), 1.19–1.63(bs, 9H), 2.02, 2.89(m, 1H, pyrr.H), 3.35–3.50(m, 2H), 3.56–3.67(dd, 1H, C$_6$-H), 3.70–3.85(m, 1H, pyrr.H), 3.95–4.10(bs, 2H, CHCH$_2$OH), 4.25–4.31(m, 2H, C$_5$-H and CH$_3$CHOH), 4.60(t, 1H, pyrr.H)

EXAMPLE 17

Preparation of
(1R,5S,6S)-6-[(R)-1-hydroxyethyl]-2-[(3S,5S)-5-(1-
(2-methylpropyl)-2-hydroxyethyl)-(S)-aminocarbonyl)-
pyrrolidine-3-ylthio]-1-methylcarbapenem-
3-carboxylic acid The procedure was carried out according to the Example 3 and the used thiol compound was (2S,4S)-2-(1-isobutyl-2-hydroxyethyl-(R)-aminocarbonyl)-4-mercapto-1-p-nitrobenzyloxycarbonyl pyrrolidine.

$^1$H-NMR(D$_2$O): δ0.85–0.96(m, 6H, 2CH$_3$), 1.19–1.63(bs, 9H), 2.02, 2.89(m, 1H, pyrr.H), 3.35–3.50(m, 2H), 3.56–3.67(dd, 1H, C$_6$-H), 3.70–3.85(m, 1H, pyrr.H), 3.95–4.10(bs, 2H, CHCH$_2$OH), 4.25–4.31(m, 2H, C$_5$-H and CH$_3$$\underline{CHOH}$) 4.62(t, 1$\overline{H, pyrr.H}$)

Preparation of
(1R,5S,6S)-6-[(R)-1-hydroxyethyl]-2-[(3S,5S)-5-(
1-(2-methylpropyl)-2-hydroxyethyl)-(S)-aminocarbonyl)-
pyrrolidine-3-yl-thio]-1-methylcarbapenem-
3-carboxylic acid The procedure was carried out according to the Example 3 and the used thiol compound was (2S,4S)-2-(1-isobutyl-2-hydroxyethyl-(S)-aminocarbonyl)- 4-mercapto-1-p-nitrobenzyloxycarbonyl pyrrolidine.

$^1$H-NMR(D$_2$O): δ0.85–0.96(m, 6H, 2CH$_3$), 1.19–1.63(bs, 9H), 2.20, 2.89(m, 1H, pyrr.H), 3.53–3.50(m, 2H), 3.56–3.67(dd, 1H, C$_6$-H), 3.70–3.85(m, 1H, pyrr.H), 3.95–4.10(bs, 2H, CHCH$_2$OH), 4.25–4.31(m, 2H, C$_5$-H and CH$_3$CHOH), 4.62(t, 1H, pyrr.H)

EXAMPLE 19

Preparation of (1R,5S,6S)-6-[(R)-1-hydroxyethyl]-2-[(3S,5S)-5-(2-(1,3-dihydroxypropyl)-aminocarbonyl)pyrrolidine-3-ylthio]-1-methylcabapenem- 3-carboxylic acid The procedure was carried out according to the Example 3 and the used thiol compound was (2S,4S)-2-(di-(2-hydroxyethyl)aminocarbonyl)-4-mercapto-1-p-nitrobenzyloxycarbonyl pyrrolidine.

$^1$H-NMR(D$_2$O): δ1.22(d, 3H, β-CH$_3$), 1.33(d, 3H, CH$_3$CHOH), 2.10, 2.99(m, 1H, pyrr.H), 3.35—3.58(m, 2H, C$_6$-H and C$_1$-H), 3.63–3.88(m, 6H, pyrr.H and CH$_2$OH), 4.09(m, 1H, pyrr.H), 4.25–4.31(m, 2H, C$_5$-H and CH$_3$CHOH), 4.55(t, 1H, pyrr.H)

EXAMPLE 20

Preparation of (1R,5S,6S)-6-[(R)-1-hydroxyethyl]-2-[(3S,5S)-5-(2,3-dihydroxypropyl)aminocarbonyl)pyrrolidine-3-ylthio]-1-methylcarbapenem-3-carboxylic acid The procedure was carried out according to the Example 3 and the used thiol compound was (2S,4S)-2-(di-(2,3-di(hydroxy)propyl aminocarbonyl)-4-mercapto-1-p-nitrobenzyloxycarbonyl pyrrolidine.

$^1$H-NMR(D$_2$O): δ1.22(d, 3H, β-CH$_3$), 1.30(d, 3H, CH$_3$CHOH), 1.40–1.71(bs, 2H, piperidine H), 1.90–2.10(bs, 3H, piperdine H and pyrrolidine C$_4$H), 3.15(m, 1H, pyrrolidine C$_4$-H), 3.30(dq, 1H, C$_1$-H), 3.35–3.55(bs, 5H, piperidine H and C$_6$-H) 3.95–4.15(bs, 2H, pyrrolidine C$_2$-H), 4.25–4.30(m, 2H, C$_5$-H and CH$_3$CHOH), 4.85(m, 1H, pyrrolidine C$_5$-H)

EXAMPLE 21

Preparation of (1R,5S,6S)-6-[(R)-1-hydroxyethyl]-2-[(3S,5S)-5-(4-hydroxypiperidinyl-N-carbonyl)pyrrolidine-3-ylthio]-1-methylcarbapenem- 3-carboxylic acid The procedure was carried out according to the Example 3 and the used thiol compound was (2S,4S)-2-(4-hydroxy piperidinyl-N-carbonyl)-4-mercapto-1-p-nitrobenzyloxycarbonyl pyrrolidine.

$^1$H-NMR(D$_2$O): δ1.18(d, 3H, β-CH$_3$), 1.20(d, 3H, CH$_3$CHOH), 1.50–1.85(bs, 5H, piperidine H), 3.40(dd, 1H, C$_6$-H), 3.45–3.90(bs, 3H, piperidine H), 4.25(dd, 1H, C$_5$-H), 4.85(m, 1H, pyrrolidine C$_5$-H)

EXAMPLE 22

Preparation of (1R,5S,6S)-6-[(R)-1-hydroxyethyl]-2-[(3S,5S)-5-(2-hydroxymethylpiperidinyl-N-carbonyl)pyrrolidine-3-ylthio]-1-methylcarbapenem- 3-carboxylic acid The procedure was carried out according to the Example 3 and the used thiol compound was (2S,4S)-2-(2-hydroxymethylpiperidinyl-N-carbonyl)-4-mercapto-1-p-nitrobenzyloxycarbonyl pyrrolidine.

$^1$H-NMR(D$_2$O): δ1.18(d, 3H, β-CH$_3$), 1.20(d, 3H, CH$_3$CHOH), 1.50–1.85(bs, 6H, piperdine H), 3.05(d, 2H, CH$_2$OH), 3.40(dd, 1H, C$_6$-H), 3.45–3.90(bs, 3H, piperidine H), 4.25(dd, 1H, C$_5$-H), 4.85(m, 1H, pyrrolidine C$_5$-H)

EXAMPLE 23

Preparation of (1R,5S,6S)-6-[(R)-1-hydroxyethyl]-2-[(3S,5S)-5-(2-hydroxyethylpiperidinyl-N-carbonyl)pyrrolidine-3-ylthio]-1-methylcarbapenem-3-carboxylic acid The procedure was carried out according to the Example 3 and the used thiol compound was (2S,4S)-2-(2-hydroxyethylpiperidinyl-N-carbonyl)-4-mercapto-1-p-nitrobenzyloxycarbonyl pyrrolidine.

$^1$H-NMR(D$_2$O): δ1.19(d, 3H, β-CH$_3$), 1.22(d, 3H, CH$_3$CHOH), 1.50–1.85(bs, 8H, piperidine H and CH$_2$CH$_2$OH), 3.10(t, 2H, CH$_2$OH), 3.35(dq, 1H, C$_1$-H), 4.80(m, 1H, pyrrolidine C$_5$-H)

EXAMPLE 24

Preparation of (1R,5S,6S)-6-[(R)-1-hydroxyethyl]-2-[(3S,5S)-5-(3,3-dimethylpiperidinyl-N-carbonyl)pyrrolidine-3-ylthio]-1-methylcarbapenem-3-carboxylic acid The procedure was carried out according to the Example 3 and the used thiol compound was (2S,4S)-2-(3-dimethylpiperdinyl-N-carbonyl)-4-mercapto-1-p-nitrobenzyloxycarbonyl pyrrolidine.

$^1$H-NMR(D$_2$O): δ0.90(d, 6H, 2CH$_3$), 1.20(d, 3H, β-CH$_3$), 1.25(d, 3H, CH$_3$CHOH), 1.35–1.65(bs, 5H, piperidine H), 2.85(m, 1H, pyrrolidine C$_4$-H), 3.33(dq, 1H, C$_1$-H), 3.45(dd, 1H, C$_6$-H), 4.20(dq, 1H, CH$_3$CHOH), 4.25(dd, 1H, C$_5$-H), 4.82(m, 1H, pyrrolidine C$_5$-H)

EXAMPLE 25

Preparation of (1R,5S,6S)-6-[(R)-1-hydroxyethyl]-2-[(3S,5S)-5-(3-methylpiperidinyl-N-carbonyl)pyrrolidine-3-ylthio]-1-methylcarbapenem- 3-carboxylic acid The procedure was carried out according to the Example 3 and the used thiol compound was (2S,4S)-2-(3-methylpiperidinyl-N-carbonyl)-4-mercapto-1-p-nitrobenzyloxycarbonyl pyrrolidine.

$^1$H-NMR(D$_2$O): δ0.90(d, 3H, —CH$_3$), 1.20(d, 3H, β-CH$_3$), 1.28(d, 3H CH$_3$CHOH), 1.50–1.85(bs, 5H, piperidine H), 3.15(m, 1H, pyrrolidine C$_4$-H), 3.35(dq, 1H, C$_1$-H), 3.50(dd, 1H, C$_6$-H), 3.95–4.15(bs, 4H, piperidine H), 4.25(dd, 1H, C$_5$-H), 4.85(m, 1H, pyrrolidine C$_5$-H)

EXAMPLE 26

Preparation of (1R,5S,6S)-6-[(R)-1-hydroxyethyl]-2-[(3S, 5S)-5-(1,2,5,6-tetrahydropyridinyl-N-carbonyl)pyrrolidine-3-ylthio]-1-methylcarbapenem-3-carboxylic acid The procedure was carried out according to the Example 3 and the used thiol compound was (2S,4S)-2-(1,2,5,6-tetrahydropyridinyl-N-carbonyl)-4-mercapto-1-p-nitrobenzyloxycarbonyl pyrrolidine.

$^1$H-NMR(D$_2$O): δ1.25(d, 3H, β-CH$_3$), 1.35(d, 3H, CH$_3$CHOH), 1.60–1.78(bs, 2H, piperidine H), 3.12(m, 1H, pyrrolidine C$_4$-H), 3.40(dq, 1H, C$_1$-H), 3.55(dd, 1H, C$_6$-H), 4.28(dd, 1H, C$_6$-H), 4.85(m, 1H, pyrrolidine C$_5$-H), 5.80–5.95(t, piperidine CH=CH)

EXAMPLE 27

Preparation of (1R,5S,6S)-6-[(R)-1-hydroxyethyl]-2-[(3S,5S)-5-(2-hydroxymethylpyrrolidinyl-N-carbonyl)pyrrolidine-3-ylthio]-1-methylcarbapenem-3-carboxylic acid The procedure was carried out according to the Example 3 and the used thiol compound was (2S,4S)-2-(2-hydroxymethylpyrrolidinyl-N-carbonyl)-4-mercapto-1-p-nitrobenzyloxycarbonyl pyrrolidine.

$^1$H-NMR(D$_2$O): δ1.25(d, 3H, β-CH$_3$), 1.33(d, 3H, CH$_3$CHOH), 1.85–2.15(bs, 4H, piperidine H), 3.10(m, 3H, pyrrolidine C$_4$-H and CH$_2$OH), 3.40(dq, 1H, C$_1$-H), 3.50(dd, 1H, C$_6$-H), 4.28(dd, 1H, C$_6$-H), 4.88(m, 1H, pyrrolidine C$_5$-H)

EXAMPLE 28

Preparation of (1R,5S,6S)-6-[(R)-1-hydroxyethyl]-2-[(3S,5S)-5-(homopiperidinyl-N-carbonyl)pyrroline-3-ylthio]-1-methylcarbanenem-3-carboxylic acid The procedure was carried out according to the Example 3 and the used thiol compound was (2S,4S)-2-(homopiperidinyl-N-carbonyl)-4-mercapto-1-p-nitrobenzyloxycarbonyl pyrrolidine.

$^1$H-NMR(D$_2$O): δ1.20(d, 3H, β-CH$_3$), 1.25(d, 3H, CH$_3$CHOH), 1.55–1.80(bs, 8H, homopiperidine H), 3.10(m, 1H, pyrrolidine C$_4$-H), 3.34(dq, 1H, C$_1$-H), 3.55(dd, 1H, C$_6$-H), 4.28(dd, 1H, C$_5$-H), 4.85(m, 1H, pyrrolidine C$_5$-H)

EXAMPLE 29

Preparation of (1R,5S,6S)-6-[(R)-1-hydroxyethyl]-2-[(3S,5S)-5-(thiazolyl-N-carbonyl)pyrrolidine-3-ylthio]-1-methylcarbapenem-3-carboxylic acid The procedure was carried out according to the Example 3 and the used thiol compound was (2S,4S)-2-(thiazolyl-)carbonyl-4-mercapto-1-p-nitrobenzyloxycarbonyl pyrrolidine.

$^1$H-NMR(D$_2$O): δ1.23(d, 3H, β-CH$_3$), 1.30(d, 3H, CH$_3$CHOH), 2.08, 3.55(m, 1H, pyrr.H), 3.33(dq, 1H, C$_1$-H), 3.38–3.55(bs, 5H), 3.98–4.10(bs, 2H, pyrr.H), 4.25–4.31(m, 2H), 4.45(m, 1H, pyrr.H)

EXAMPLE 30

Preparation of (1R,5S,6S)-6-[(R)-1-hydroxyethyl]-2-[(3S,5S)-5-(2-hydroxymethylthiazolyl-N-carbonyl)pyrrolidine-3-ylthio]-1-methylcarbapenem-3-carboxylic acid The procedure was carried out according to the Example 3 and the used thiol compound was (2S,4S)-2-(2-hydroxymethylthiazolyl-N-carbonyl-4-mercapto-1-p-nitrobenzyloxycarbonyl pyrrolidine.

$^1$H-NMR(D$_2$O): δ1.23(d, 3H, β-CH$_3$), 1.30(d, 3H, CH$_3$CHOH), 2.08, 3.55(m, 1H, pyrr.H), 3.10–3.21(bs, 2H), 3.33(dq, 1H, C$_1$-H), 3.38–3.55(bs, 5H), 3.98–4.10(bs, 2H, pyrr.H), 4.25–4.31(m, 2H), 4.45(m, 1H, pyrr.H)

EXAMPLE 31

Preparation of (1R,5S,6S)-6-[(R)-1-hxdroxyethyl]-2-[(3S,5S)-5-((S-methyl-thiazolyl-N-carbonylpyrrolidine)-3-ylthio]-1-methylcarbapenem-3-carboxylic acid The procedure was carried out according to the Example 2 using the thiol compound of Example 30.

$^1$H-NMR(D$_2$O): δ1.23(d, 3H, β-CH$_3$), 1.30(d, 3H, CH$_3$CHOH), 2.08, 3.55(m, 1H, pyrr.H), 3.10(s, 3H), 3.33(dq, 1H, C$_1$-H), 3.38–3.55(bs, 5H), 3.98–4.10(bs, 2H, pyrr.H), 4.25–4.31(m, 2H), 4.45(m, 1H, pyrr.H)

What is claimed is:

1. 1-β-methyl-2-thiolic carbapenem derivatives having the following formula (I):

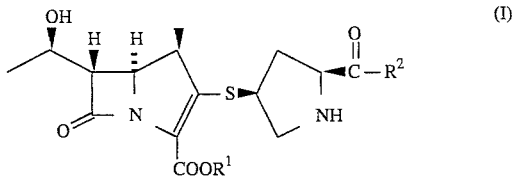

in the formula (I), R$^1$ denotes anion and R$^2$ denotes N-(S-alkylthiomorpholinylium) of following formula ① or N-(S-alkylthiazolium) cation of following formula ②,

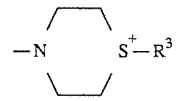

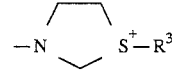

(In the above formula ① and ②, R$^3$ denotes methyl or low alkyl group of C$_2$–C$_4$).

2. 1-β-methyl-2-thiolic carbapenem derivatives (I) according to claim 1, wherein optical isomer configuration of said carbapenem ring is (1R,5S,6S,8R).

3. 1-β-methyl-2-thiolic carbapenem derivatives (I) according to claim 1, wherein optical isomer configuration of thiol derivatives substituted on C-2 position of carbapenem ring is (3S,5S).

* * * * *